(12) United States Patent
Hood et al.

(10) Patent No.: US 8,920,847 B2
(45) Date of Patent: Dec. 30, 2014

(54) MENSTRUAL FLUID SIMULANT

(75) Inventors: William Hollis Hood, Cincinnati, OH (US); Marsha Jean Spears, Fort Thomas, KY (US); William Joseph Worley, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1145 days.

(21) Appl. No.: 12/651,602

(22) Filed: Jan. 4, 2010

(65) Prior Publication Data

US 2010/0126256 A1 May 27, 2010

Related U.S. Application Data

(63) Continuation of application No. 11/406,614, filed on Apr. 19, 2006, now Pat. No. 7,659,372.

(51) Int. Cl.
| | | |
|---|---|---|
| *A61K 35/12* | (2006.01) | |
| *A61K 35/14* | (2006.01) | |
| *A61K 35/18* | (2006.01) | |
| *A61K 38/01* | (2006.01) | |
| *A61K 35/24* | (2006.01) | |
| *A61K 36/54* | (2006.01) | |

(52) U.S. Cl.
CPC .................. *A61K 35/14* (2013.01); *A61K 35/18* (2013.01); *A61K 38/014* (2013.01); *A61K 15/40* (2013.01); *A61K 35/24* (2013.01); *A61K 36/54* (2013.01)
USPC ........................................... 424/520; 424/529

(58) Field of Classification Search
USPC ................................. 424/520, 529
See application file for complete search history.

(56) References Cited

U.S. PATENT DOCUMENTS

| | | | |
|---|---|---|---|
| 2,824,092 A * | 2/1958 | Thompson | 530/354 |
| 4,321,924 A | 3/1982 | Ahr | |
| 4,923,454 A | 5/1990 | Seymour et al. | |
| 5,356,626 A | 10/1994 | Yeo et al. | |
| 5,545,155 A * | 8/1996 | Hseih et al. | 604/378 |
| 5,643,240 A | 7/1997 | Jackson et al. | |
| 5,849,805 A * | 12/1998 | Dyer | 521/64 |
| 5,883,231 A * | 3/1999 | Achter et al. | 530/362 |
| 6,586,653 B2 | 7/2003 | Graeme, III et al. | |
| 6,953,775 B2 | 10/2005 | Burruano et al. | |
| 7,687,681 B2 | 3/2010 | Di Luccio et al. | |
| 2005/0059942 A1 | 3/2005 | Krautkramer et al. | |
| 2010/0174260 A1 | 7/2010 | Di Luccio et al. | |

FOREIGN PATENT DOCUMENTS

| | | |
|---|---|---|
| DE | 19915716 C1 | 10/2000 |
| EP | 0 668 066 B1 | 7/1999 |
| EP | 1 136 824 A1 | 9/2001 |
| EP | 1 247 508 A2 | 10/2002 |
| EP | 1 252 873 A2 | 10/2002 |
| EP | 1 547 559 A1 | 6/2005 |
| JP | 2004-344532 A | 12/2004 |
| WO | WO 98/09662 A1 | 3/1998 |
| WO | WO 98/51250 A1 | 11/1998 |

OTHER PUBLICATIONS

Kočevar-Nared et al., Comparative rheological investigation of crude gastric mucin and natural gastric mucus. Biomaterials, vol. 18 (1997) pp. 677-681.*
Jumel et al., Rapid size distribution and purity analysis of gastric mucus glycoproteins by size exclusion chromatography/multi angle laser light scattering. International Journal of Biological Macromolecules, vol. 18 (1996) pp. 133-139.*
French Group of Producers of Articles for Sanitary and Domestic Uses, "'Retention Products' in Articles for Infant or Feminine Hygiene and for Incontinence", "Proposal of the Technical Committee of the Group", Jun. 1991.
Flood, J.A., et al., "A toroid model for in vitro investigations of toxic shock syndrome toxin-1 production", Journal of Microbiological Methods, 57 (2004) 283-288.
Owen, Derek H., et al., "A Vaginal Fluid Simulant", Elsevier Science Inc., 1999, pp. 91-95.
Burruano, Bríd T., et al., "Synthetic cervical mucus formulation", ScienceDirect, Contraception, vol. 66, Issue 2, Aug. 2002, pp. 137-140.
http://www.mpbio.com/advanced_search_result.php?name=&catalog=155742&cas=&ec&s, MUCIN from MP Biochemicals Catalog, accessed Jun. 22, 2009.
Definition of music from Stedman's medical Dictionary, 1995, Houghton Mifflin Co., http://dictionary.reference.com/browse/mucus, accessed Jan. 8, 2009.
Bell et al., "The causes of the non-coagulability of normal menstrual blood and of pathological clotting", J. Pathology and Bacteriology 18" 462-8 (1914).
PCT International Search Report dated Apr. 10, 2007.

* cited by examiner

*Primary Examiner* — Jon P Weber
*Assistant Examiner* — Kara Johnson
(74) *Attorney, Agent, or Firm* — Andres E. Velarde; Amanda T. Barry

(57) ABSTRACT

Menstrual fluid simulants may consistently emulate the physical characteristics of real menstrual fluid, including but not limited to, viscosity, stringiness, surface tension and size and concentration of particulate matter. In addition, the constituents comprising the menstrual fluid simulants may be changed in order to mimic the variations in real menstrual fluid observed from woman to woman and from an individual woman over time. The menstrual fluid simulants are of use in the testing of personal care absorbent products.

6 Claims, No Drawings

MENSTRUAL FLUID SIMULANT

CROSS REFERENCE TO RELATED APPLICATION

This application is a continuation of U.S. patent application Ser. No. 11/406,614, filed Apr. 19, 2006 now U.S. Pat. No. 7,659,372.

FIELD OF THE INVENTION

Menstrual fluid simulants of use for in vitro testing of feminine hygiene products.

BACKGROUND OF THE INVENTION

Personal care absorbent products abound in the market place. Such products are used by persons of all ages and include diapers, training pants, adult incontinence articles and feminine hygiene products such as tampons and sanitary napkins. Personal care absorbent products are often subjected to efficacy testing during the product development phase as well as to substantiate advertising claims directed to the commercialized product.

Efficacy testing may be completed in vivo and/or in vitro. In vivo tests may require panelists to wear a product for a finite time, and then return the used product for data collection and evaluation. In vivo testing can be costly and time-consuming. Moreover, in vivo testing exposes the data collector to the potential risk of contact with bodily fluids and associated pathogens. In vitro testing can offer a higher degree of experimental control and precision than in vivo testing. For these reasons, in vivo test procedures and artificial body exudates have been developed for in vitro testing. For instance, the developers of feminine hygiene products have liquid substitutes for menstrual fluid that are used in laboratory testing and efficacy demonstrations.

Fluid properties such as surface tension, viscosity, stringiness, and the size and concentration of particulate matter may affect the interaction of any fluid with the porous surfaces and absorbent materials that form today's highly engineered, high performance feminine hygiene products. Many of the conventional artificial menstrual fluids do not emulate all of these properties. For example, some artificial fluids are liquid solutions with all of the solids dissolved therein. Artificial fluids that lack solids tend to be absorbed more readily than real menstrual fluid, which is a multi-phase suspension of particulate matter in an aqueous liquid. Some artificial fluids do not contain blood despite observations that real menstrual fluid has properties similar to blood particularly during periods of high flow. Other artificial fluids currently in use do not contain mucus or other ingredients necessary to impart the type of stringy viscoelastic behavior typical of real menstrual fluid.

In order for in vitro testing of absorbent feminine hygiene products to provide data that are most directly comparable with in vivo data, the menstrual fluid simulant should closely emulate the physical properties of real menstrual fluid. Therefore, a menstrual fluid simulant that comprises the properties of real menstrual fluid is desirable.

The fluid properties of real menstrual fluid are highly variable from woman to woman and may even vary with regard to an individual woman over the course of her menstrual period. Therefore, a menstrual fluid simulant with a composition that can be adjusted to emulate variations in the properties of real menstrual fluid is also desirable.

SUMMARY OF THE INVENTION

The present invention provides improved menstrual fluid simulants for use in in vitro testing. Real menstrual fluid contains blood and mucus, yet conventional menstrual fluid simulants are typically formulated without either component. Some conventional simulants utilize reconstituted mucin powder to simulate the properties of mucus. When fresh mucus is heated and dried to make mucin powder, the glycoproteins contained therein may degrade, irreversibly altering its physicochemical properties. As such, mucus collected in its hydrated state directly from an animal has better solubility and purity than reconstituted mucin powder. It has surprisingly been found that mucus substitutes with physicochemical properties analogous to real mucus may be formulated without using mucin powder. It has surprisingly been found that by using these mucus substitutes and/or mucus collected directly from an animal, in combination with a blood product, the menstrual fluid simulants of the present invention more accurately replicate the physical properties of real menstrual fluid than conventional simulants. In addition, it has surprisingly been found that the formulation of the menstrual fluid simulants of the present invention can intentionally be altered to mimic the naturally occurring variation observed in the physical properties of real menstrual fluid.

One embodiment of the menstrual fluid simulant has a general formulation comprising:
  1. a blood product;
  2. mucus or a mucus substitute to increase viscosity; and
  3. buffer to control pH and electrolyte concentration.

Some single additives may also be added which serve the purpose of increasing both viscosity and stringiness. However, separate ingredients may be added to enable a degree of independent control over viscosity or stringiness. For example, a high molecular weight polymer may be added to increase the stringiness of the menstrual fluid simulant.

In some embodiments, the invention is directed to menstrual fluid simulants comprising from about 5% to about 90% by weight of a blood product; and from about 1% to about 30% by weight of mucus.

In some embodiments, the invention is directed to menstrual fluid simulants comprising: from about 5% to about 90% by weight of a blood product; and from about 1% to about 30% by weight of a mucus substitute.

In some embodiments, the present invention is directed to menstrual fluid simulants comprising: from about 5% to about 90% of a blood product; from about 1% to about 30% by weight of a gelatin solution; from about 1% to about 30% by weight of an aqueous buffering agent; and from about 1% to about 5% of a high molecular weight water-soluble polymer such as polyacrylamide.

The present invention provides a menstrual fluid simulant that may consistently emulate the physical characteristics of real menstrual fluid, including but not limited to, viscosity, stringiness, surface tension and size and concentration of particulate matter. In addition, the constituents comprising the menstrual fluid simulant may be intentionally changed in order to mimic the variations in real menstrual fluid observed from woman to woman and from an individual woman over time. These and additional advantages will be more apparent in view of the following detailed description.

DETAILED DESCRIPTION

The term "blood product" as used herein refers to blood, reconstituted blood, synthetic blood, red blood cells and combinations thereof. The term "blood" is a general term, which encompasses both whole blood and blood that may have had constituents removed from it, such as plasma for example. Whole blood is blood collected from an animal from which no constituent, such as plasma, has been removed. Reconstituted blood comprises red blood cells that are separated from the other components found in whole blood, which is then reconstituted with plasma, aqueous buffer, or combinations thereof. The red blood cells may be separated from the other components found in the whole blood via any method known in the art including, but not limited to, centrifugation (for example at 3000 revolutions per minute for 30 minutes), in which case the red blood cells are referred to as "packed" red blood cells. If reconstituted red blood cells ("packed" or otherwise) are used in the menstrual fluid simulant (hereinafter referred to as MFS), the red blood cells may be used "as is" or they may be reconstituted to a concentration that is consistent with that found in the whole blood of the animal from which the red blood cells are collected to form reconstituted blood. Synthetic blood may be any synthetic blood known in the art that approximates the physical properties of human blood, such as being comprised of particles that are similar in size to human red blood cells for example.

As used herein, the term "stringy" is interchangeable with the term "ropy" and refers to being viscous and capable of being drawn into a thread.

When used herein in relation to liquid compositions, the terms "%" and "percent" refer to the quantity by weight of a component as a percentage of the total weight of the liquid composition, unless otherwise indicated.

I. Menstrual Fluid Properties

The present menstrual MFS is formulated on the basis of recent advances in the understanding of menstrual fluid rheology. It has been found that properties such as viscosity, stringiness, surface tension and the size and concentration of particulate matter can affect the interaction of menstrual fluid with the porous surfaces and absorbent materials that comprise feminine hygiene articles.

1. Viscosity

Viscosity may affect the acquisition rate of menstrual fluid into absorbent structures, such as feminine hygiene products. For example, if menstrual fluid viscosity is high, the acquisition rate may be low and initially the relative amount of fluid available for sorption onto the contacting surface may be high.

Real menstrual fluid viscosity may range from several centipoises (cP) to several hundred cP. The viscosity of menstrual fluid is highly dependent on shear rate and temperature. The viscosity of the present MFS is typically measured at a shear rate of 20 $sec^{-1}$ at 25° C., using an AR-2000 rotational viscometer from TA Instruments, Newcastle, Del., with the fluid between parallel plates separated by a distance of 500 to 1000 microns. The viscosity of the present MFS may be altered by varying the content of mucus, mucus substitute, rheological modifiers and combinations thereof.

2. Stringiness

When a liquid exists as a thin layer between two adjacent surfaces and those surfaces are separated, some liquids break cleanly while other liquids appear to stretch and form "strings" many times the initial liquid thickness. Strings have been observed in biological fluids and are hypothesized to result from the presence therein of high molecular weight species. Human nasal discharge is an example of a viscoelastic fluid that exhibits stringiness under certain conditions. Nasal mucus can range from being watery to gelatinous depending on the concentration of mucus in the solution. Saliva normally has a low degree of elasticity, but as water evaporates on the lips, the concentration of salivary mucus rises and stringiness or even slight adhesion of the lips may occur.

Real menstrual fluid has varying degrees of stringiness that can be observed or measured by lifting a glass rod from a collected sample. The elasticity of menstrual fluid has a rate dependent effect on the way the fluid spontaneously spreads on a surface, is wicked into capillaries in fibrous structures, and on the way fluid distributes between surfaces that are in intermittent contact. If fluid elasticity is very high, it may exhibit a yield stress behavior where there is no spontaneous absorption into a capillary structure. Thus the elasticity of real menstrual fluid is an important determinant in how it interacts with a feminine hygiene product. The stringiness of the present MFS may be altered by varying content of mucus, mucus substitute, rheological modifiers and combinations thereof

3. Surface Tension

The surface tension of a fluid impacts its ability to wet the surface of a feminine hygiene product as well as the ability of the product to absorb and retain the fluid. Real menstrual fluid is a multi-component liquid which may contain, among other things, varying amounts of fatty acids, alcohols and glycoproteins, which may have a surfactant-like character that reduces the effective surface tension of the menstrual fluid. The surface tension of real menstrual fluid tends to be similar to blood, but with a greater degree of variability than blood. Water and conventional fluid simulants that are simple aqueous solutions have a surface tension of approximately 73 dynes/cm, whereas the blood plasma that is found in real menstrual fluid has a surface tension closer to about 50 dynes/cm. Consequently, it is believed that on a given surface, blood will not bead up as much as water and will tend to spread out to a greater extent.

On the forgoing bases, the MFS of the present invention is formulated with a blood product to more closely approximate the surface tension of real menstrual fluid.

4. Size and Concentration of Particulate Matter

Particulate matter is commonly found in real menstrual fluid, and may comprise mucoid and other proteinaceous cell membranes, red blood cells and agglomerations thereof, the contents of ruptured red blood cells, microorganisms and combinations thereof. Particulate matter can affect the absorbency of a feminine hygiene article, such as a feminine napkin or tampon, by blocking the pores and capillaries that form the article's surface. The size and concentration of particulate matter in real menstrual fluid may vary widely.

To simulate the particulate matter found in real menstrual fluid, a blood product is used in the MFS of the present invention. Blood, reconstituted blood and red blood cells, packed or otherwise, may be used as they may comprise red blood cells, agglomerations of red blood cells, as well as ruptured blood cells and their contents. Synthetic blood may be used if it comprises particulate matter that approximates that found in mammalian blood. In addition to the blood product, mucus, mucin powder, mucus substitute and combinations thereof, is used in the MFS of the present invention to provide further particulate matter. For example, unfiltered gastric mucin solutions contain hundreds to thousands of particles per cubic mm, and the particles in mucin solution range from 5 micron in diameter to 50 microns in diameter. Pig stomach mucus also contains insoluble material and in its natural state is opaque due to particulates present. As a result, the MFS of the present invention simulates the microscopic appearance and behavior of real menses.

II. Menstrual Fluid Simulant Compositions

The MFSs of the present invention have surprisingly been found to emulate the physical properties of real menstrual fluid including, but not limited to, viscosity, stringiness, surface tension and size and concentration of particulate matter. Moreover, it has surprisingly been found that rheological modifiers may be added to the mixture to fine tune these properties in order to mimic the variations in properties observed in real menstrual fluid.

In some embodiments of the present invention, the MFS is formulated with a blood product, mucus and an aqueous buffering agent. In other embodiments, the MFS is formulated with a blood product and a mucus substitute with properties similar to real mucus. In some embodiments, the physical characteristics of the MFS may be modified through the addition of rheological modifiers.

1. Blood Products

Menstrual fluid is comprised of blood. The blood content in menstrual fluid may vary from individual to individual and may vary with respect to a given individual over the course of her period. For instance, blood content in menstrual fluid may be lower at the beginning and end of the menstrual period than at the time of highest flow. In order to mimic the physical and biochemical properties of real menstrual fluid at the heaviest day of flow, or at any other time during the average woman's period, the percentage by weight of blood product content of the present MFS may be from about 5% to about 90%, from about 20% to about 85%, from about 30% to about 80%, or even from about 50% to about 75%. Blood products of use include, but are not limited to: blood; reconstituted blood; red blood cells; synthetic blood; and combinations thereof.

To mimic the physical and biochemical properties of real menstrual fluid, human blood is ideal. However, the use of human blood may be costly and can require strict biohazard precautions to ensure safe handling. Consequently, other types of mammalian blood are of use in the MFS of the present invention.

Mammalian blood is comprised of red blood cells (RBC) which vary in size depending upon their source. On average, human RBC vary in size from about 8 to about 12 microns (μm) in diameter; swine RBC vary in size from about 6 to about 10 μm in diameter; sheep RBC are about 4.5 μm in diameter; bovine RBC are about 5.5 μm in diameter; feline RBC are about 5.8 μm in diameter; canine RBC are about 7 μm in diameter; equine RBC are about 5.7 μm in diameter; and goat RBC are about 4 μm in diameter. Thus, a number of different types of mammalian blood, and combinations thereof, are of use in the present invention. For example, swine, sheep, bovine, feline, canine, equine, goat blood and combinations thereof may be of use as safe, less costly alternatives to human blood. Synthetic human blood and/or synthetic human RBC may also be of use. A non-limiting example of a synthetic blood simulant is described in EP 1 136 824 A1, which is assigned to ProRheo.

If the MFS of the present invention is used immediately after the blood comprising it is collected from a mammal, or if the blood product comprising the MFS does not contain factors that will cause it to coagulate, then coagulation of the blood may not be an issue. If it is an issue however, then the blood product will have been treated so that it will not coagulate. This treatment may be any treatment known in the art, including, but not limited to, defibrinating the blood to remove the clotting fibrous materials, the addition of anticoagulant chemicals and combinations thereof.

2. Mucus

Real menstrual fluid comprises blood and vaginal mucus. Mucus is an elastic hydrogel of high molecular weight, typically over about 180 kilo Daltons (kDa), and in its natural form is comprised of a solution of glycoproteins and water. Glycoprotein-based mucus has been identified as a component in real menstrual fluid that is related to the fluid's characteristic elasticity (which is measured by stringiness). Real mucus is typically absent in conventional menstrual fluid simulants, and reconstituted mucin powder has often been used in its place. Mucin powder is conventionally made by grinding, heating and drying animal stomach linings; these processes may degrade the glycoproteins, lowering their effective molecular weight and irreversibly altering their physicochemical properties. As such, reconstituted mucin powder may not provide the stringiness provided by mucus that is collected in its hydrated state directly from an animal. It has surprisingly been found that by using real mucus in combination with a blood product, the MFSs of the present invention more accurately replicate the physical properties of real menstrual fluid than do conventional simulants.

Mucus may be collected from various sources. Non-limiting examples of mucus sources include pigs, hag fish, eels and combinations thereof. Pig stomach mucus is an abundant source of mucus that is chemically similar to human vaginal mucus. Harvested pig stomach mucus may be added to the MFS of the present invention to provide stringiness as well as to increase viscosity at any shear rate.

The stringiness and viscosity of the present MFS may be varied by changing the mucus content. The MFS may comprise a percentage by weight of mucus solution of: from about 1% to about 30%; or from about 1% to about 20%; or from about 2% to about 15%; or even from about 6% to about 8%.

3. Mucus Substitutes

Lower cost alternatives to real mucus may be of use in the MFS of the present invention. The mucus substitutes of the present invention have surprisingly been found to closely approximate the fluid properties of real mucus, particularly as compared to reconstituted mucin powder. Non-limiting examples of mucus substitutes of use in the present invention include: Carbopol® (a Goodrich Chemical Company (Cleveland, Ohio) trade name for a family of water-soluble acrylic acid polymers distributed by numerous specialty chemical suppliers), sassafras powder, yam powder, psyllium extracts, xanthum gum, guar gum, gelatin and mixtures thereof Carbopol® 934 is one particular Carbopol® that is of use that is distributed by Noveon, Inc., Cleveland, Ohio.

When gelatin is used as a mucus substitute in some embodiments of the present invention, the MFS may further be comprised of rheology modifiers. In some embodiments, the rheological modifiers may be a water soluble polymer. In some embodiments, the water soluble polymer is anionic-substituted polyacrylamide. From the standpoint of its solubility and chemical functional groups, the anionic-substituted polyacrylamide has similarities to biological polymers. Because of its high molecular weight and stability, a very small amount may be added to the MFS to precisely control the stringiness of the fluid. In one embodiment of the present invention, the polyacrylamide polymer may be present in the MFS in a quantity from: about 25 to about 600 parts per million (PPM); about 50 to about 400 ppm; or even from about 150 to about 300 ppm. The addition of very small amounts of anionic-substituted polyacrylamide may increase the viscosity of the MFS slightly, but it increases its elasticity drastically. This approach may be favored over those that, while they would work, would require adding larger quantities of less effective polysaccharides or proteins to achieve stringiness. Adding large quantities of these additives could alter the bulk chemistry of the MFS.

4. Buffering Agent

To mimic the physical and biochemical properties of real menstrual fluid, an aqueous buffering agent may be of use in the present MFS. The buffering agent may serve several purposes. For example, the buffering agent may maintain the proper biological ionic strength and buffering capacity of real menstrual fluid, and the buffering agent may act as a diluent, such as for the mucus and any mucin powder (used as a rheological modifier) that is present. Any aqueous buffering agent that provides the osmotic pressure of blood and thereby prevents the rupture of RBC may be of use.

The aqueous buffering agent may be a solution containing approximately equal amounts of a conjugate acid/base pair. The aqueous buffering agent may contain salt and have a pH that is from: about 4 to about 9; or 5 to 8; or even 6 to 8. Non-limiting examples of aqueous buffers include: phosphate buffer saline (PBS), which has a pH of about 7.2; potassium hydrogen phthalate; and potassium phthalate.

5. Rheological Modifiers

The stringiness of real menstrual fluid is highly variable. Some menstrual fluid samples have no apparent stringiness. Rheological modifiers may be added to the menstrual fluids of the present invention in order to fine tune their stringiness. Any suitable rheological modifier is of use. Non-limiting examples of rheological modifiers include water soluble polymers selected from the group consisting of: polyvinyl alcohols; hydroxyalkyl starches; hydroxyethyl celluloses; hydroxypropyl celluloses; carboxylated latexes; hydroxylated latexes; alginates; polyacrylates; natural gums; modified gums (such as guar gum); polyethylene oxide; polypropylene oxide; proteins (such as gelatin); glycoprotein; polysaccharides (such as starch, extracts from plants, such as okra and sassafras); capsular polysaccharides; polyacrylamides; polyvinylpyrrolidine; cellulose derivatives; mucin powder; nucleic acids; and combinations thereof. Nucleic acids are selected from the group consisting of ribonucleic acid (RNA), deoxyribonucleic acid (DNA), RNA fragments, DNA fragments, and mixtures thereof. Other high molecular weight proteins that are naturally found in mucus may also be of use.

In some embodiments of the present invention, mucin powder may also be added to increase the stringiness of the MFS. Mucin powder may be reconstituted using any suitable means. In some embodiments, a 20% gastric mucin concentrate is made by reconstituting the mucin powder in phosphate buffer, then concentrating it. The resulting gastric mucin concentrate may then be added to the MFS to a percentage by weight of: from about 1% to about 20%; from about 2% to about 15%; or even from about 3% to about 14%.

In some embodiments of the present invention, water soluble polymers may be added to increase the stringiness of the MFS. Any suitable water soluble polymer may be of use. Non-limiting examples of water soluble polymers of use include: flocculants such as Superfloc A-150, from Cytec Industries, West Paterson, N.J., USA.

III. Methods of Making MFS

I. Protocol to Prepare Pig Stomach Mucus:
1. Collect pig stomachs at slaughter, wash them with tap water and store in a freezer set at about minus 30° C.
2. When ready to harvest the mucus, remove the stomachs from the freezer and allow them to thaw overnight.
3. Open the stomachs and wash them under running tap water to remove any feed.
4. Pin the stomach open on a corkboard and collect the mucus from the stomach lining by scraping it with a plastic spatula.
5. Transfer the collected mucus to a previously tared container.
6. Add an equal volume of a phosphate buffer saline solution (PBS) with a pH of about 7.2 to the mucus and mix the resulting mixture with a plastic spatula.
7. Homogenize the mixture using a kitchen blender at medium speed for about 2 minutes.
8. Centrifuge the homogenized mixture at 6000 revolutions per minute for 1 hour at 4° C.
9. Remove the supernatant and place it in dialysis tubing with a 12-14,000 molecular weight cut-off, and dialyze against distilled, deionized water for 24 hours in a refrigerator (set at about 40° C.+/−4° C.) in order to remove excess salt.
10. Concentrate the mucus using the same type of dialysis tubing in a bed of an absorbent gelling material at around 40° C.
11. Remove the concentrated mucus from the dialysis tubing and keep it at minus 20° C. until use. The mucus may be thawed and refrozen. Visually inspect the thawed mucus in order to make sure that it is homogeneous.

Similar methods are of use for concentrating mucus recovered from hag fish and eels.

II. Protocol to Prepare Plant-Derived Mucus Substitutes

To prepare plant-derived mucus substitutes from sources including, but not limited to, sassafras, yams or psyllium, the following protocol is used. The mucus-like components are extracted from a plant or its vegetable using PBS with a pH from about 4.0 to about 10.0. The portion of the plant or its vegetable that contains the mucus-like component is added to the PBS as a finely ground powder or in small pieces in increments that would result in a mixture of between about 0.1 and about 20% by weight depending on the individual mucus-like containing component. For example, powder from sassafras leaves, yams and/or psylliums is added to the PBS. The mixture is heated to between about 40° C. and about 120° C. and held at temperature for up to an hour. The resulting mixture is then filtered through a 10 μm nominal filter bag to eliminate any large particles. Upon cooling, the resulting mucus substitute is then mixed with the other components comprising the MFS of the present invention.

IV. Examples

Exemplary formulations of the present invention are listed in the following tables. The amount of each component present in each MFS formulation is provided as a percentage of the total weight of the MFS. Table 1 provides examples of MFSs comprising mucus. Table 2 provides examples of MFSs comprising mucus substitutes.

TABLE 1

MFS Formulations Comprising Mucus

| Example | Swine whole blood | Burro whole blood | Swine Packed Red blood cells | Concentrated pig stomach mucus | Gastric mucin concentrate | Saline/Phosphate buffer | Okra extract solution | 2% Acrylamide in saline | 1% Acrylamide in saline | Serum | Totals |
|---|---|---|---|---|---|---|---|---|---|---|---|
| 1 | 71.4% | | | 7.1% | 14.4% | | 7.1% | | | | 100.0% |
| 2 | 83.3% | | | 8.3% | 8.4% | | | | | | 100.0% |
| 3 | 83.3% | | | 8.3% | | | 8.3% | | | | 100.0% |
| 4 | 69.0% | | | 6.9% | 6.9% | 17.2% | | | | | 100.0% |
| 5 | 69.0% | | | 6.9% | 3.4% | 20.7% | | | | | 100.0% |
| 6 | 71.4% | | | 7.1% | 3.6% | 17.9% | | | | | 100.0% |
| 7 | 71.4% | | | 7.1% | 1.9% | 19.6% | | | | | 100.0% |
| 8 | 74.1% | | | 7.4% | | 18.5% | | | | | 100.0% |
| 9 | 83.3% | | | 16.7% | | 0.0% | | | | | 100.0% |
| 10 | 67.8% | | | 6.8% | 3.4% | 16.9% | | 5.1% | | | 100.0% |
| 11 | 69.6% | | | 7.0% | 3.1% | 17.4% | | 3.0% | | | 100.0% |
| 12 | 69.6% | | | 7.0% | | 21.9% | | 1.5% | | | 100.0% |
| 13 | 72.2% | | | 7.2% | 1.8% | 18.0% | | 0.8% | | | 100.0% |
| 14 | 71.1% | | | 7.1% | 2.5% | 17.8% | | | 1.5% | | 100.0% |
| 15 | 50.0% | | | | 7.9% | 42.1% | | | | | 100.0% |
| 16 | | 50.0% | | | 7.9% | 42.1% | | | | | 100.0% |
| 17 | | | 27% | 7.1% | 2.5% | 17.8% | | | 1.5% | 44% | 100.0% |
| 18 | | | 28% | 6.8% | 3.4% | 16.7% | | 5.1% | | 40% | 100.0% |

TABLE 2

MFS Formulations Comprising Mucus Substitute

| Example | Swine blood | Burro blood | Sheep blood | 0.5% xanthum gum in buffer | 0.075% Carbopol® 934 in saline | 12% Gelatin in DI water | Sassafras powder | Saline/Phosphate buffer | 1% Acrylamide in saline | Totals |
|---|---|---|---|---|---|---|---|---|---|---|
| 15 | 50.0% | | | 50.0% | | | | | | 100.0% |
| 16 | 66.7% | | | | 33.3% | | | | | 100.0% |
| 17 | 80.0% | | | | 20.0% | | | | | 100.0% |
| 18 | 70.0% | | | | | 7.0% | | 21.5% | 1.5% | 100.0% |
| 19 | 70.0% | | | | | 8.0% | | 20.5% | 1.5% | 100.0% |
| 20 | 70.0% | | | | | 6.0% | | 22.5% | 1.5% | 100.0% |
| 21 | 50.0% | | | | | | 2.0% | 48.0% | | 100.0% |
| 22 | | 50.0% | | | | | 2.0% | 48.0% | | 100.0% |
| 23 | | | 50.0% | | | | 2.0% | 48.0% | | 100.0% |

The following examples, A, B and C, illustrate how the constituents comprising an MFS may be adjusted in order to replicate variations in the properties of real menstrual fluid observed from woman to woman and from an individual woman over time. Specifically, the following examples are different samples of MFSs that are made to have varying viscosities.

Example A

This MFS emulates real menstrual fluid with a viscosity that is measured as 0.020 Pa sec at 20 sec$^{-1}$.

71% Defibrinated swine blood 7.1% Pig stomach mucus 2.5% gastric mucin concentrate (27 g gastric mucin powder/450 ml PBS solution/dialyzed/concentrated)

17.8% PBS solution 1.5% of a 1% solution of Superfloc® 150 in saline

Superfloc™ 150 is an anionic high molecular weight polyacrylamide, which is available from Cytek Industries, West Paterson, N.J., USA.

Example B

This MFS emulates real menstrual fluid with a viscosity that is measured as 0.035 Pa sec at 20 sec−1.

70% Defibrinated swine blood

7% Pig stomach mucus

3% gastric mucin concentrate (27 g gastric mucin powder/450 ml PBS solution/dialyzed/concentrated)

17% PBS solution

3% of a 1% solution of Superfloc™ 150 in saline

Example C

This MFS emulates real menstrual fluid with a viscosity that is measured as 0.090 Pa sec at 20 sec−1.

69% Defibrinated swine blood

7% Pig stomach mucus

14% gastric mucin concentrate (27 g gastric mucin powder/450 ml PBS solution/dialyzed/concentrated)

7% PBS solution

3% of a 1% solution of Superfloc™ 150 in saline

IV. Methods of Testing Absorbent Feminine Hygiene Products with MFS:

The various embodiments of MFSs of the present invention are of use for in vitro testing of absorbent feminine hygiene products including, but not limited to, tampons, sanitary napkins and pantiliners. A number of performance parameters may be measured by applying the MFS to absorbent products. Non-limiting examples of such parameters include absorbent capacity, run-off or gush and strike through, which may be measured using various means including, but not limited to, visual means, gravimetric means, photographic means, using photomicrography and combinations thereof.

As discussed above, the composition of the MFSs of the present invention may be adjusted to emulate the variations in menstrual fluid properties that are observed over the course of a woman's period. Thus an absorbent feminine hygiene article could be tested for its performance over the course of a woman's period, including low flow and high flow days. For example, assuming for hypothetical purposes only that the viscosity of menstrual fluid varies inversely with the flow of menstrual fluid, a sanitary napkin could be tested for its absorbent capacity on: (1) a low flow day using the MFS from Example C that is very viscous and very stringy; (2) a medium flow day using the MFS from Example B that is less viscous and very stringy; and (3) a high flow day using the MFS from Example A that is the least viscous and less stringy.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A menstrual fluid simulant comprising:
    a. from about 5% to about 90% by weight of a blood product; and
    b. from about 1% to about 16.7% by weight of mucus comprising a molecular weight of over about 180 kilo Daltons;
    c. from 1% to about 5% of a rheological modifier comprising polyacrylamide and optionally mucin powder, water soluble polymers, nucleic acids and fragments thereof, or mixtures thereof;
    wherein the mucus is collected in its hydrated state directly from an animal.

2. The menstrual fluid simulant according to claim 1, further comprising from about 1% to about 30% by weight of an aqueous buffering agent.

3. The menstrual fluid simulant according to claim 1, wherein said blood product is selected from the group consisting of: swine blood; burro blood; human blood; sheep blood; bovine blood; synthetic blood; reconstituted blood; red blood cells and mixtures thereof.

4. The menstrual fluid simulant according to claim 1, wherein said mucus is selected from the group consisting of: pig stomach mucus; hag fish mucus; eel mucus; and mixtures thereof.

5. The menstrual fluid simulant according to claim 1, wherein said simulant comprises from about 5% to about 8.3% by weight of said mucus.

6. The menstrual fluid simulant according to claim 1, wherein said simulant comprises from about 5% to about 25% by weight of said buffering agent.

* * * * *